United States Patent
Arakawa et al.

(10) Patent No.: US 8,294,894 B2
(45) Date of Patent: Oct. 23, 2012

(54) PARTICLE COUNTER

(75) Inventors: Akira Arakawa, Kyoto (JP); Takahiro Mori, Kyoto (JP); Tsunehiro Inoue, Ominhachiman (JP)

(73) Assignee: Shimadzu Corporation, Kyoto (JP)

( * ) Notice: Subject to any disclaimer, the term of this patent is extended or adjusted under 35 U.S.C. 154(b) by 435 days.

(21) Appl. No.: 12/626,370

(22) Filed: Nov. 25, 2009

(65) Prior Publication Data

US 2010/0134796 A1    Jun. 3, 2010

(30) Foreign Application Priority Data

Nov. 28, 2008  (JP) ................................. 2008-305369

(51) Int. Cl.
   *G01N 21/00*  (2006.01)

(52) U.S. Cl. ...................................................... 356/337

(58) Field of Classification Search ........... 356/335–344
   See application file for complete search history.

(56) References Cited

U.S. PATENT DOCUMENTS

| | | | | |
|---|---|---|---|---|
| 4,277,170 A | * | 7/1981 | Miles | 356/141.3 |
| 4,739,177 A | * | 4/1988 | Borden | 250/574 |
| 4,864,127 A | * | 9/1989 | Brame | 250/253 |
| 4,928,537 A | * | 5/1990 | Liu et al. | 73/863.86 |
| 5,192,870 A | * | 3/1993 | Batchelder et al. | 250/574 |
| 5,247,188 A | * | 9/1993 | Borden | 250/574 |
| 5,300,780 A | * | 4/1994 | Denney et al. | 250/342 |
| 5,943,130 A | * | 8/1999 | Bonin et al. | 356/336 |
| RE38,025 E | * | 3/2003 | Skunes et al. | 356/400 |
| 6,781,688 B2 | * | 8/2004 | Kren et al. | 356/237.4 |

FOREIGN PATENT DOCUMENTS

| | | |
|---|---|---|
| JP | 06-026823 A | 2/1994 |
| JP | 07-306133 A | 11/1995 |

* cited by examiner

*Primary Examiner* — Layla Lauchman
*Assistant Examiner* — Jarreas C Underwood
(74) *Attorney, Agent, or Firm* — Sughrue Mion, PLLC

(57) ABSTRACT

The present invention provides a particle counter capable of accurately discriminating the signal of scattered light by real particles from the background light noise, and furthermore, capable of detecting smaller particles than conventional particle counters. The particle counter according to the present invention includes: a light irradiator for emitting light to the measurement area 40 in a vacuum state or in a near vacuum state; a scattered light detector 32 for detecting scattered light generated when the light is delivered to the measurement area 40; a discriminator 18 for determining whether or not a particle exists in the measurement area 40 by comparing the detection signal of the scattered light detector 32 and a predetermined discrimination threshold; a vacuum gauge 12 for measuring the pressure of the measurement area 40; and the threshold setting unit 16 for setting a discrimination threshold in accordance with the pressure of the measurement area 40.

4 Claims, 3 Drawing Sheets

PARTICLE COUNTER

The present invention relates to a particle counter for counting the number of particles such as solid particles contained in the emission gas of a semiconductor manufacturing equipment and other apparatuses.

BACKGROUND OF THE INVENTION

Dust particles generated during the process of producing semiconductors degrade the products. Therefore, semiconductor manufacturing equipments are normally equipped with a particle counter for counting in real time the number of particles generated in the process chamber.

The particle counter is generally provided in an exhaust duct from the process chamber, and includes: a light source for emitting a laser light to the measurement area in the exhaust duct; a detector for detecting the light scattered by a particle on which the laser light is irradiated; a discriminator for determining whether or not a particle exists by comparing the detection signal of the detector with a predetermined specific discrimination threshold; and other units.

The detector detects not only the light scattered by particles that pass the measurement area but also the light scattered by molecules of gas such as oxygen (or air), nitrogen, and other elements existing as a background gas in the measurement area. This is because molecules of gas such as oxygen, nitrogen, and other elements are very small particles and scatter light when irradiated.

When the background noise of the scattered light due to the gas molecules as just described is large, an accurate discrimination is difficult between the signal of the scattered light by real particles and that of the background light noise. If the gas molecules existing in a measurement area are further abundant, the intensity of the background light may be stronger than that of the light scattered by the smallest particles to be measured, which prevents the detection of small-size particles.

Given such factors, a method to decrease the background light noise has been proposed in which scattered lights are detected by a detector composed of a large number of sensing elements, i.e. having a large number of pixels (refer to Patent Document 1). This is based on the principle that narrowing the detection area of one sensing element reduces the background light noise, so that small-size particles can be detected.

Patent Document 1: Japanese Unexamined Patent Application Publication No. H06-26823

SUMMARY OF THE INVENTION

The magnitude of the background light noise changes depending on the number of gas molecules existing in the measurement area. However, in conventional particle counters, the number of gas molecules existing in the measurement area is not taken into consideration, and the signal of scattered light by real particles is discriminated from the background light noise based on a specific discrimination threshold.

The problem to be solved by the present invention is to provide a particle counter capable of accurately discriminating the signal of light scattered by real particles from the background light noise, and furthermore, capable of detecting smaller particles than before.

The present invention achieved to solve the aforementioned problem provides a particle counter including:

a) a light emitter for emitting a light to a measurement area in a vacuum state or in a near vacuum state;
b) a scattered light detector for detecting a scattered light generated when a light is delivered to the measurement area;
c) a vacuum measurement means for measuring the degree of vacuum of the measurement area;
d) a threshold setting unit for setting a discrimination threshold in accordance with the degree of vacuum of the measurement area; and
e) a discriminator for determining whether or not a particle exists in the measurement area by comparing the detection signal of the scattered light detector and the discrimination threshold.

Another aspect of the present invention provides a particle counter including:

a) a light emitter for emitting a light to a measurement area in a vacuum state or in a near vacuum state;
b) a scattered light detector for detecting scattered light generated when a light is delivered to the measurement area and for converting into an electrical signal;
c) a threshold setting unit for setting the discrimination threshold based on a time average of the electrical signal; and
d) a discriminator for determining whether or not a particle exists in the measurement area by comparing the electrical signal and the discrimination threshold.

It is preferable that, for the aforementioned "time average of the electrical signal", the time average of the electrical signal of light scattered by particles flowing through the measurement area over the time twice or more of the peak width is taken.

The scattered light detector detects not only the light scattered by particles existing in the measurement area, but also the light scattered by the molecules of gas such as nitrogen, oxygen, and other elements existing in the measurement area, i.e. the background light noise. The number of molecules of gas such as nitrogen, oxygen, and other elements existing in the measurement area is proportional to the pressure of the measurement area, and the intensity of the background light noise is proportional to the number of gas molecules. Therefore, the intensity of the background light noise is proportional to the pressure. The degree of vacuum of the measurement area is measured by the vacuum measurement means.

In the present invention, whether or not a particle exists is determined based on the discrimination threshold which is set in accordance with the degree of vacuum of the measurement area, or with the time average of the electrical signal of scattered light. Therefore, it is possible to avoid erroneously detecting a noise signal by molecules of gas such as nitrogen, oxygen, and other elements as a signal of scattered light of particles. Since the background light noise is smaller as the vacuum is higher (i.e. closer to the true vacuum), the discrimination threshold can be set smaller, enabling the detection of smaller particles.

EXPLANATION OF THE NUMERALS

| | |
|---|---|
| 10 | Detector |
| 12 | Vacuum Gauge |
| 13 | Signal Processor |
| 16 | Threshold Setting Unit |
| 18 | Threshold Discriminator |
| 20 | Counter |
| 22 | Exhaust Pipe |
| 24 | Light Incident Window |
| 26 | Light Exit Window |
| 28 | Light Irradiator |
| 281 | Light Source |
| 30 | Detection Window |
| 32 | Scattered Light Detector |
| 34 | Condenser Lens |
| 40 | Measurement Area |

DETAILED DESCRIPTION OF PREFERRED EMBODIMENTS

Hereinafter, some embodiments of the present invention are described in detail with reference to the attached drawings.

Figure 1:
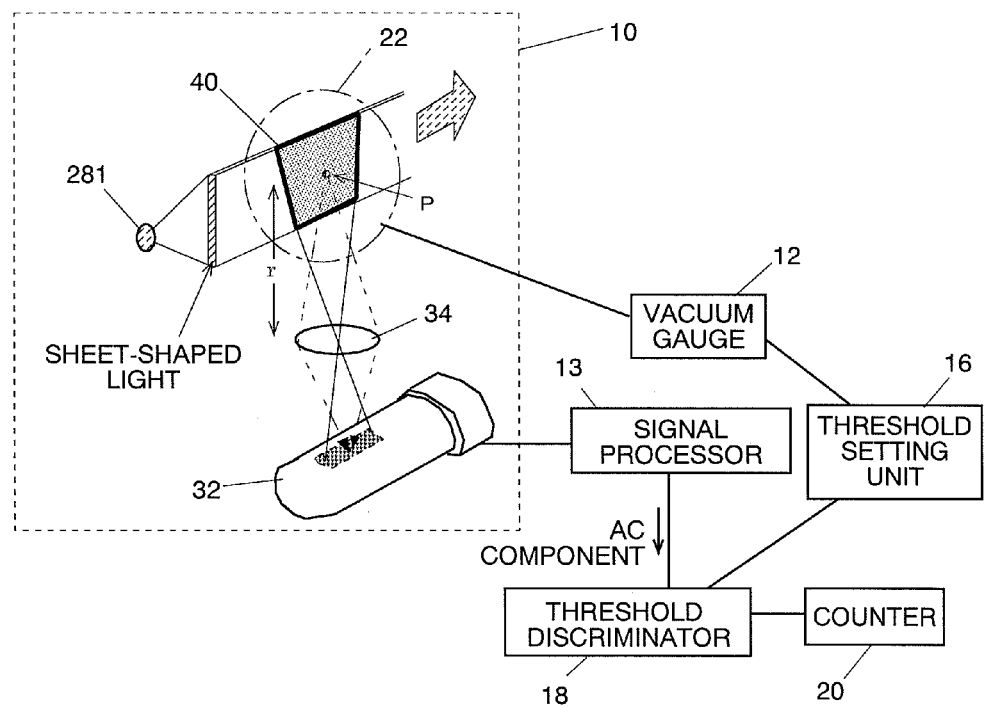
FIG. 1 is a schematic configuration diagram of an entire particle counter according to the first embodiment of the present invention.

FIG. 1 is a schematic configuration diagram of the particle counter according to the first embodiment of the present invention. The particle counter 1 is composed of a detector 10, a vacuum gauge 12, a signal processor 13, a threshold setting unit 16, a threshold discriminator 18, a counter 20, and other units.

Figure 2:
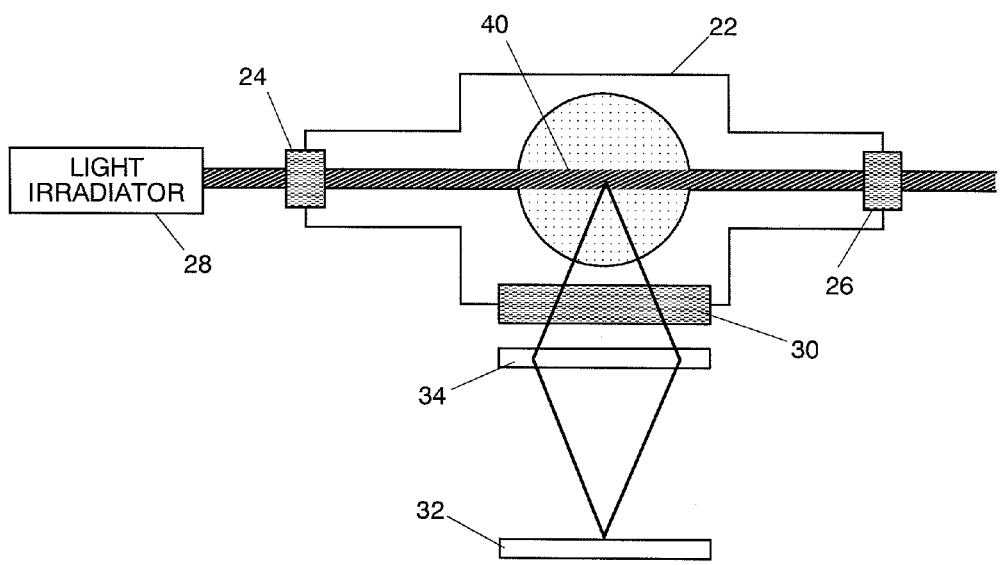
FIG. 2 is a schematic diagram of a light detector provided on an exhaust pipe.

As illustrated in FIGS. 1 and 2, the detector 10 is provided on the exhaust pipe 22 of a semiconductor manufacturing equipment for example. The inside of the exhaust pipe 22 is in a vacuum state or in a near vacuum state, and a particle P flows in the direction perpendicular to the paper plane (e.g. from the front to the back of the paper plane) of FIG. 2.

The detector 10 has: a light incident window 24 and a light exit window 26 which are placed on the opposite walls of the exhaust pipe 22; a light irradiator 28 for delivering a laser light through the light incident window 24 toward the light exit window 26; a detection window 30 provided on a wall of the exhaust pipe 22 lying normal to the direction substantially perpendicular to the direction of the irradiation of the laser light; a scattered light detector 32 for detecting the scattered light that has passed through the detection window 30; a condenser lens 34 placed between the detection window 30 and the scattered light detector 32; and other components.

The light irradiator 28 is composed of: a light source 281 which is a semiconductor laser element or other illuminant; and a lens (not shown) for converting the laser light of light source 281 into sheet-shaped light. The sheet-shaped light emitted from the light irradiator 28 enters the exhaust pipe 22 through the light incident window 24, and passes through the inside of the exhaust pipe 22 (which is in vacuum). Accordingly, the light is thrown to a rectangular sheet-like measurement area 40 in the exhaust pipe 22, and particles flowing through the measurement area 40 generate scattered light. A portion of the scattered light generated in the measurement area 40 passes through the detection window 30 and is converged to the scattered light detector 32 by the condenser lens 34.

The scattered light is detected and converted to an electrical signal by the scattered light detector 32, and the electrical signal is provided to a signal processor 13 From the electrical signal including pulse signals representing the scattered lights, the signal processor 13 extracts the alternate-current (AC) component. The AC component is obtained by subtracting the direct-current (DC) component from the electrical signal of the scattered light. The DC component is obtained by integrating the electrical signal from the scattered light detector 32 with a time constant sufficiently longer than the duration of the pulse signal of the scattered light, and represents the time average of the electrical signal. In the present embodiment, the DC component is the time average over 100 msec, for example.

The AC component output from the signal processor 13 is sent to the discriminator 18 to be compared with a threshold. When the AC component exceeds the threshold, the discriminator 18 determines that a particle has passed and sends a determination signal to the counter 20. The counter 20 counts the number of the particles that have passed through the measurement area 40 in a predetermined time.

The degree of vacuum of the inside of the exhaust pipe 22 is measured by the vacuum gauge 12, and the threshold setting unit 16 sets the discrimination value based on the degree of vacuum. The threshold setting unit 16 may set the discrimination value that follows the change in the degree of vacuum, or may set the discrimination value based on the average of the degree of vacuum over a predetermined time.

The detection signal of the scattered light detector 32 is now described. The light entering the scattered light detector 32 includes not only the light scattered by particles but also the background light due to the molecules of gas such as oxygen, nitrogen, and other elements existing in the measurement area 40. Gas of oxygen, nitrogen, and other elements is also composed of a group of very small particles, and scatters light when light is thrown.

Accordingly, the detection signal of the scattered light detector 32 includes components of the light (or background noise) scattered by the gas such as oxygen, nitrogen and other elements, to which the component of the light scattered by particles are added.

For example, when a non-polarized plane wave (having an intensity of $I_0$) is thrown to an isolated particle in vacuum, where the particle has the radius a which is sufficiently smaller than the wavelength of light, the ratio [intensity of scattered light $I_{scat}$/intensity of thrown light $I_0$] at distance r from the particle can be obtained by the following equation (1) based on the Rayleigh theory:

$$\frac{I_{scat}}{I_{0\_unpol}} = \frac{I_1 + I_2}{2} = \frac{8\pi^4 a^6}{r^2 \lambda^4}\left(\frac{n^2-1}{n^2+2}\right)(1+\cos^2\theta) \quad (1)$$

where a is the radius of the particle, r is the distance from the scattered particle, $\lambda$ is the wavelength of light, n is the refractive index of the particle, and $\theta$ is the angle between the incident light and scattered light.

The intensity of light scattered by the gas such as oxygen, nitrogen, and other elements is proportional to the value calculated by the intensity of light scattered by one gas molecule (which is calculated by equation (1)) multiplied by the number of gas molecules. Since the number of gas molecules existing in the measurement area 40 is proportional to the pressure, the intensity of background light by gas molecules is proportional to the pressure.

For example, the intensity of light scattered by a large number of nitrogen molecules and the intensity of light scattered by a particle are compared, where the diameter of a nitrogen gas molecule is supposed to be 0.2 nm and that of the particle is 200 nm. Equation (1) shows that the intensity of scattered light is proportional to the sixth power of the diameter of a particle. Under the aforementioned suppositions, the diameter of the particle is 1000 ($=10^3$) times larger than the nitrogen molecules, so that the intensity due to the particle is $10^{18}$ times stronger than that due to the nitrogen molecules. Supposing, for example, that the pressure is 1 atm and the volume of the detection area is 0.2 ml, the number of molecules existing in the area is $5.357 \times 10^{18}$ ($=6 \times 10^{23}/22.4 \times 0.2 \times 10^{-3}$). This indicates that the light scattered by the molecules of nitrogen at 1 atm is greater than the light scattered by a particle of 200 nm.

In order to avoid erroneously determine the light scattered by gas molecules as that scattered by a particle, it is necessary to set the discrimination threshold higher than the intensity of light scattered by gas molecules. On the other hand, a large discrimination threshold prevents the detection of small particles because a particle of smaller diameter generates smaller scattered light intensity.

The intensity of the background light by gas molecules existing in the measurement area 40 is uniquely determined when the pressure of the measurement area 40 is known. Hence, the discrimination threshold may be set to a value with which the background light (or its voltage signal) uniquely determined by the degree of vacuum of the measurement area 40 is not counted as light scattered by a particle. This enables the detection of a particle as small as possible.

Figure 3:
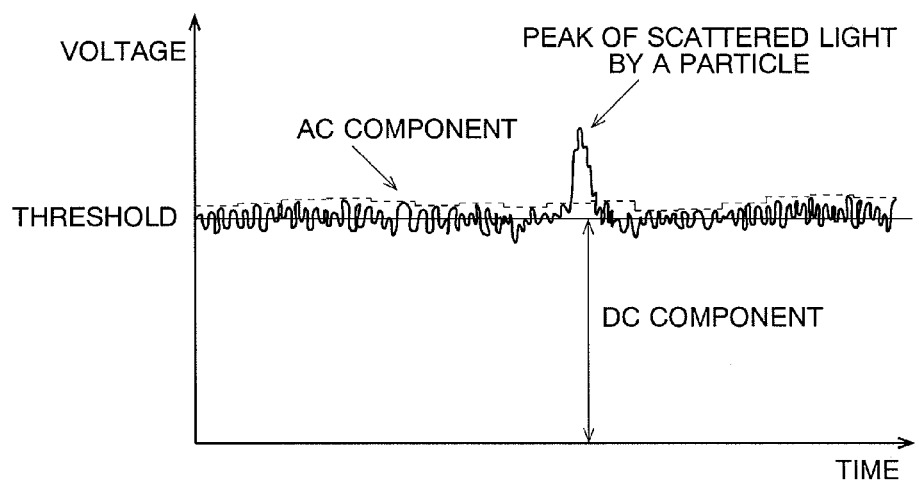
FIG. 3 is a diagram illustrating a voltage signal of scattered light.

FIG. 3 illustrates the relationship among the electrical signal of the scattered light, the AC component, the DC component and the discrimination threshold. As illustrated in FIG. 3, the AC component, which is the subtraction of the DC component from the electrical signal of the scattered light, is the fluctuation component caused by the scattered light. The DC component of the scattered light represents the background light component that changes according to the change in the degree of vacuum (pressure) of the measurement area 40.

Since the fluctuation of light is generally proportional to the square root of the intensity of the light, the AC component, of the background light is proportional to the square root of the pressure. Regarding this factor, in the present embodiment, the threshold setting unit 16 sets an appropriate threshold value in accordance with the square root of the pressure in the exhaust pipe 22, or the pressure in the measurement area 40, which is detected by the vacuum gauge 12. When the pressure is low, the background light noise is small: accordingly a small value will be set as the discrimination threshold.

The result of an experiment will be shown in which particles in the measurement area were counted by using the above described particle counter.

Figure 4:
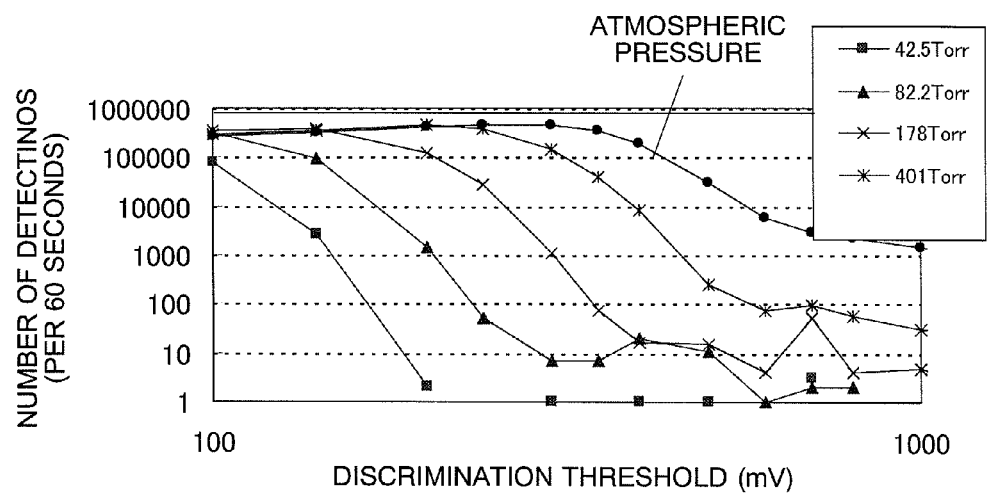
FIG. 4 is a diagram illustrating the relationship between the discrimination threshold and the number of counts at different degrees of vacuum.

FIG. 4 is a diagram illustrating the relationship between the discrimination threshold and the number of counts of the counter 20 in the cases when nitrogen gas is flown in the exhaust pipe 22 at a flow rate of 1 m/sec at different pressures. The pressure was changed at five levels (42.5 Torr, 82.2 Torr, 178 Torr, 401 Torr, and the atmospheric pressure (760 Torr)). Higher pressure means larger number of nitrogen molecules present. In FIG. 4, the horizontal axis represents the discrimination threshold (mV), and the vertical axis represents the number of counts of the counter 20 per 60 seconds. The "number of counts" in FIG. 4 means the number that the counter 20 counted on the light scattered by nitrogen gas molecules, i.e. the number in which nitrogen gas molecules were erroneously detected as particles.

As is apparent from FIG. 4, the number of counts decreases as the discrimination threshold increases. For the same discrimination threshold, the lower the pressure becomes (i.e. closer to the true vacuum), the smaller the number of counts becomes. Therefore, it is understood that setting an appropriate discrimination threshold based on the pressure can prevent an erroneous detection of the molecules of gas, such as nitrogen, as a particle.

In order to detect the light scattered by a particle and not to detect the light scattered by gas such as oxygen and nitrogen, it is appropriate to set the discrimination threshold so that the number of counts by the light scattered by the gas such as oxygen and nitrogen is equal to or less than 10 per 60 seconds.

At the pressure of 42.5 Torr, for example, the number of counts with the discrimination thresholds of 100 mV and 140 mV is both larger than 10 per 60 seconds, and the number of counts with the discrimination thresholds between 200 mV and 1000 mV is from zero to three per 60 seconds. These experiments indicate that the discrimination threshold of 200 mV is appropriate at the pressure of 42.5 Torr.

At the pressure of 82.2 Torr, the number of counts with the discrimination thresholds from 100 mV to 240 mV is always larger than 10 per 60 seconds, and the number of counts with the discrimination thresholds from 300 mV to 1000 mV is from zero to 19 per 60 minutes. Although the numbers of counts with the discrimination thresholds of 400 mV and 500 mV are larger than 10 per 60 seconds, considering detection errors, the discrimination threshold of 300 mV is appropriate at the pressure of 82.2 Torr.

Figure 5:
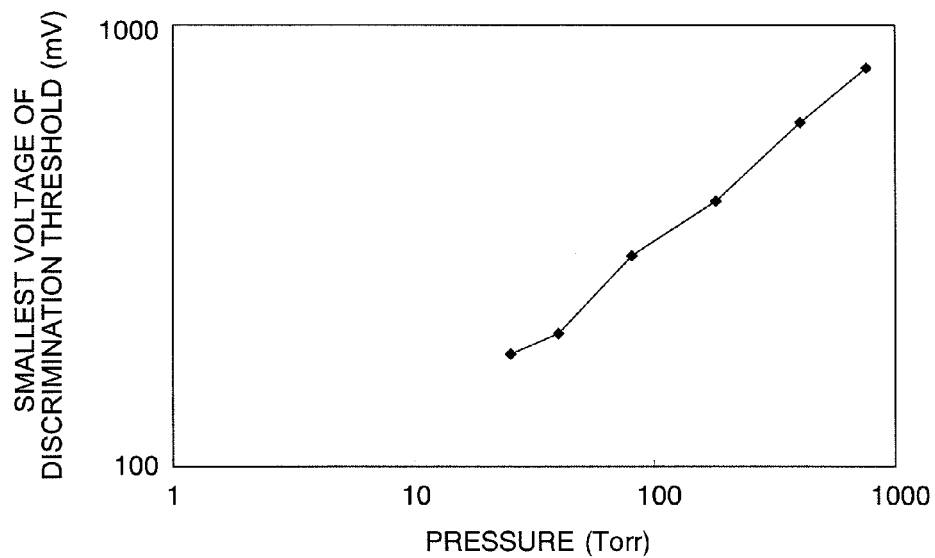
FIG. 5 is a diagram illustrating the relationship between the degree of vacuum and the smallest voltage of discrimination threshold.

FIG. 5 illustrates the relationship between the discrimination threshold with which the number of counts due to nitrogen gas molecules is equal to or less than 10 and the pressure. In FIG. 5, the horizontal axis represents the pressure (Torr) and the vertical axis represents the discrimination threshold (the smallest voltage of discrimination threshold with which the number of counts is equal to or less than 10). At the pressure of 401 Torr and at the atmospheric pressure, the number of counts does not become 10 or less due to residual impurities contained in the nitrogen gas. Hence, the discrimination threshold with which the number of counts becomes equal to or less than 10 was obtained by extrapolating the line on which the number of counts rapidly decreases. As a result, the smallest discrimination threshold at the pressure of 401 Torr and at the atmospheric pressure was approximately 600 mV and approximately 800 mV, respectively.

When the diameter of the smallest particle detectable at 800 mV, which is the discrimination threshold at the atmospheric pressure, is a, the diameter of the smallest particle detectable at 200 mV, which is the discrimination threshold at 42.5 Torr, is $(200/800)^{1/6} \times a = 0.79 \times a$, according to equation (1). That is, if the discrimination threshold is changed from 800 mV to 200 mV, the smallest diameter of detectable particles decreases to 79%. This shows that decreasing the discrimination threshold can reduce the diameter of the smallest detectable particle.

FIG. 5 is a co-logarithmic chart in which both the horizontal axis and the vertical axis are logarithmically represented. The slope of the line indicating the relationship between the pressure and the smallest discrimination threshold in FIG. 5 is about 0.5. This shows that the smallest discrimination threshold is proportional to the half power, i.e. square root, of the pressure. Therefore, by changing the discrimination threshold proportional to the square root of the pressure as in the present embodiment, the number of counts by the scattered light of nitrogen gas can be suppressed to 10 or less per 60 seconds, and thus, the diameter of the smallest detectable particle can be decreased.

Figure 6:
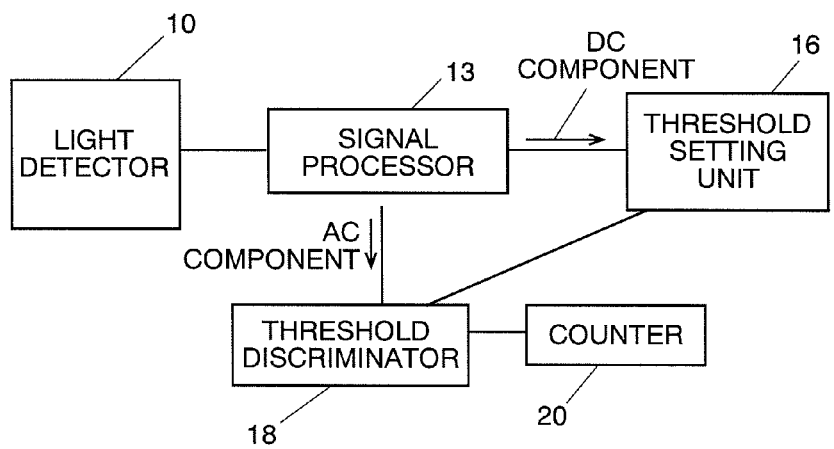
FIG. 6 is a configuration diagram of an entire particle counter according to the second embodiment of the present invention.

FIG. 6 illustrates the configuration of the second embodiment of the present invention. The following explanation is made only for the part different from the first embodiment. In the second embodiment, the signal processor 13 divides the electrical signal into DC component and AC component, and sends them out separately. The AC component output from the signal processor 13 is sent to the threshold discriminator 18, the DC component to the threshold setting unit 16.

As previously described, the DC component is obtained by integrating the electrical signal from the scattered light detector 32 with a time constant sufficiently longer than the duration of the pulse signal of the light scattered by a particle. The AC component is obtained by subtracting the DC component from the electrical signal from the scattered light detector 32.

The threshold setting unit 16 sets a value proportional to the square root of the DC component as the discrimination threshold. This is based on the principle that the intensity of light scattered by gas such as oxygen and nitrogen is proportional to the DC component and the fluctuation of light is proportional to the square root of the intensity of the light, so that the background light noise is proportional to the square root of the DC component.

What is claimed is:

1. A particle counter comprising:
   a) a light emitter for emitting a light to a measurement area in a vacuum state or in a near vacuum state;
   b) a scattered light detector for detecting scattered light generated when a light is delivered to the measurement area;
   c) a vacuum measurement means for measuring a degree of vacuum of the measurement area;
   d) a threshold setting unit for setting a discrimination threshold in accordance with the degree of vacuum of the measurement area; and
   e) a discriminator for determining whether or not a particle exists in the measurement area by comparing a detection signal of the scattered light detector and the discrimination threshold.

2. The particle counter according to claim 1, wherein the vacuum measurement means measures a pressure of the measurement area, and the threshold setting unit sets the discrimination threshold based on a square root of the pressure.

3. A particle counter comprising:
   a) a light emitter for emitting a light to a measurement area in a vacuum state or in a near vacuum state;
   b) a scattered light detector for detecting scattered light generated when a light is delivered to the measurement area and for converting into an electrical signal;
   c) a threshold setting unit for setting a discrimination threshold based on a time average of the electrical signal; and
   d) a discriminator for determining whether or not a particle exists in the measurement area by comparing the electrical signal and the discrimination threshold,
   wherein the threshold setting unit sets the discrimination threshold based on a square root of the time average of the electrical signal.

4. The particle counter according to claim 3, wherein the threshold setting unit takes the time average of the electrical signal over a time twice or more of a peak width.

* * * * *